(12) United States Patent
Volkart

(10) Patent No.: US 12,202,603 B2
(45) Date of Patent: Jan. 21, 2025

(54) UNMANNED AERIAL VEHICLE WITH BIOMETRIC VERIFICATION

(71) Applicant: **Global Tel*Link Corporation**, Reston, VA (US)

(72) Inventor: Mitch Volkart, Hartsburg, MO (US)

(73) Assignee: **Global Tel*Link Corporation**, Reston, VA (US)

( * ) Notice: Subject to any disclaimer, the term of this patent is extended or adjusted under 35 U.S.C. 154(b) by 0 days.

(21) Appl. No.: 18/239,867

(22) Filed: Aug. 30, 2023

(65) Prior Publication Data

US 2024/0228034 A1     Jul. 11, 2024

Related U.S. Application Data

(63) Continuation of application No. 16/807,634, filed on Mar. 3, 2020, now Pat. No. 11,794,895, which is a
(Continued)

(51) Int. Cl.
    *G01S 13/46*     (2006.01)
    *B60R 25/25*     (2013.01)
(Continued)

(52) U.S. Cl.
    CPC .......... *B64C 39/024* (2013.01); *B60R 25/25* (2013.01); *B60R 25/257* (2013.01); *B64U 20/87* (2023.01);
(Continued)

(58) Field of Classification Search
    CPC ...... G06V 20/56; G06V 20/58; G06V 20/582; G06V 20/584; G06V 20/586;
(Continued)

(56) References Cited

U.S. PATENT DOCUMENTS 6,130,705 A    10/2000   Lareau
7,106,843 B1    9/2006   Gainsboro et al.
(Continued)

FOREIGN PATENT DOCUMENTS

WO    WO 2013/107582 A1    7/2013

OTHER PUBLICATIONS

International Search Report and Written Opinion directed to related International Patent Application No. PCT/US2016/067252, dated Mar. 16, 2017; 14 pages.
(Continued)

*Primary Examiner* — Matthew C Bella
*Assistant Examiner* — Dennis Rosario
(74) *Attorney, Agent, or Firm* — Sterne, Kessler, Goldstein & Fox P.L.L.C.

(57) ABSTRACT

Disclosed herein are system, method, and computer program product embodiments for locating, identifying, and tracking a known criminal, fugitive, missing person, and/or any other person of interest. An embodiment operates by deploying an unmanned aerial vehicle, determining the mode of operation of the UAV, operating the UAV in accordance with the mode of operation of the UAV, determining whether a subject has been detected, capturing a first voice sample associated with the subject, authenticating the identity of the subject, and transmitting the GPS location of the unmanned aerial vehicle to a computing device.

20 Claims, 8 Drawing Sheets

Related U.S. Application Data continuation of application No. 14/971,891, filed on Dec. 16, 2015, now Pat. No. 10,579,863.

(51) Int. Cl.

| | | |
|---|---|---|
| *B64C 39/02* | (2023.01) | |
| *B64U 20/87* | (2023.01) | |
| *G01S 13/04* | (2006.01) | |
| *G01S 13/06* | (2006.01) | |
| *G01S 13/50* | (2006.01) | |
| *G05D 1/00* | (2006.01) | |
| *G05D 1/222* | (2024.01) | |
| *G05D 1/227* | (2024.01) | |
| *G05D 1/24* | (2024.01) | |
| *G05D 1/243* | (2024.01) | |
| *G05D 1/248* | (2024.01) | |
| *G05D 1/622* | (2024.01) | |
| *G05D 1/646* | (2024.01) | |
| *G05D 1/656* | (2024.01) | |
| *G05D 1/686* | (2024.01) | |
| *G05D 109/20* | (2024.01) | |
| *G05D 111/50* | (2024.01) | |
| *G06F 21/32* | (2013.01) | |
| *G06V 20/13* | (2022.01) | |
| *G06V 20/17* | (2022.01) | |
| *G06V 20/52* | (2022.01) | |
| *G06V 40/00* | (2022.01) | |
| *G06V 40/10* | (2022.01) | |
| *G06V 40/16* | (2022.01) | |
| *G06V 40/20* | (2022.01) | |
| *G08B 21/00* | (2006.01) | |
| *G08G 1/0968* | (2006.01) | |
| *G08G 5/00* | (2006.01) | |
| *B64U 101/00* | (2023.01) | |
| *B64U 101/30* | (2023.01) | |
| *B64U 101/55* | (2023.01) | |
| *B64U 101/56* | (2023.01) | |
| *B64U 101/57* | (2023.01) | |
| *B64U 101/60* | (2023.01) | |
| *G01C 21/16* | (2006.01) | |
| *G01S 13/66* | (2006.01) | |
| *G05D 1/667* | (2024.01) | |
| *G05D 1/689* | (2024.01) | |
| *G05D 111/00* | (2024.01) | |
| *G05D 111/10* | (2024.01) | |
| *G06V 10/62* | (2022.01) | |
| *G06V 20/58* | (2022.01) | |
| *G10L 17/00* | (2013.01) | |

(52) U.S. Cl.
CPC ............. *G01S 13/04* (2013.01); *G01S 13/06* (2013.01); *G01S 13/50* (2013.01); *G05D 1/0038* (2013.01); *G05D 1/0094* (2013.01); *G05D 1/222* (2024.01); *G05D 1/227* (2024.01); *G05D 1/2278* (2024.01); *G05D 1/24* (2024.01); *G05D 1/243* (2024.01); *G05D 1/248* (2024.01); *G05D 1/622* (2024.01); *G05D 1/646* (2024.01); *G05D 1/656* (2024.01); *G05D 1/686* (2024.01); *G06F 21/32* (2013.01); *G06V 20/13* (2022.01); *G06V 20/17* (2022.01); *G06V 20/52* (2022.01); *G06V 40/00* (2022.01); *G06V 40/15* (2022.01); *G06V 40/172* (2022.01); *G06V 40/20* (2022.01); *G08B 21/00* (2013.01); *G08G 1/096827* (2013.01); *G08G 5/0039* (2013.01); *B60R 2300/00* (2013.01); *B60W 2556/50* (2020.02); *B64U 2101/00* (2023.01); *B64U 2101/30* (2023.01); *B64U 2101/55* (2023.01); *B64U 2101/56* (2023.01); *B64U 2101/57* (2023.01); *B64U 2101/60* (2023.01); *B64U 2201/00* (2023.01); *B64U 2201/10* (2023.01); *B64U 2201/104* (2023.01); *G01C 21/1656* (2020.08); *G01S 2013/468* (2013.01); *G01S 13/66* (2013.01); *G01S 2205/09* (2020.05); *G05D 1/00* (2013.01); *G05D 1/665* (2024.01); *G05D 1/667* (2024.01); *G05D 1/689* (2024.01); *G05D 2109/20* (2024.01); *G05D 2111/00* (2024.01); *G05D 2111/10* (2024.01); *G05D 2111/14* (2024.01); *G05D 2111/58* (2024.01); *G06F 2221/2111* (2013.01); *G06T 2207/30201* (2013.01); *G06T 2207/30252* (2013.01); *G06V 10/62* (2022.01); *G06V 20/58* (2022.01); *G06V 40/16* (2022.01); *G06V 2201/07* (2022.01); *G10L 17/00* (2013.01)

(58) Field of Classification Search
CPC ...... G06V 20/588; G06V 20/52; G06V 20/53; G06V 20/54; G06V 20/50; G06V 20/17; G06V 2201/07; G06V 20/47; G06V 10/24; G06V 40/11; G06V 40/00; G06V 40/10; G06V 40/103; G06V 40/107; G06V 40/113; G06V 40/117; G06V 40/12; G06V 40/1382; G06V 40/1388; G06V 40/1394; G06V 40/14; G06V 40/15; G06V 40/155; G06V 40/16; G06V 40/161; G06V 40/162; G06V 40/164; G06V 40/165; G06V 40/166; G06V 40/167; G06V 40/168; G06V 40/169; G06V 40/171; G06V 40/172; G06V 40/173; G06V 40/174; G06V 40/175; G06V 40/176; G06V 40/178; G06V 40/179; G06V 40/18; G06V 40/20; G06V 40/23; G06V 40/25; G06V 40/28; G06V 40/30; G06V 40/33; G06V 40/37; G06V 40/40; G06V 40/45; G06V 40/53; G06V 40/50; G06V 40/55; G06V 40/58; G06V 40/60; G06V 40/63; G06V 40/67; G06V 40/70; G06V 40/13; G06V 40/1347; G06V 40/1365; G06V 10/255; G06V 2201/05; G06V 2201/08; G06V 2201/06; G06V 2201/09; G06F 2221/2111; G06F 21/32; G05B 19/41895; H04W 4/029; G06T 2207/30261; G06T 2207/30252; G06T 2207/30248; G06T 2207/30256; G06T 2207/30264; G06T 7/13; G06T 2207/10044; G06T 2207/30232; G06T 2207/30196; G06T 2207/30201; G06T 2207/30041; G06T 7/0012; G06T 7/10; G06T 19/003; G05D 1/0214; G05D 1/0202; G05D 1/0257; G05D 1/0231; G05D 1/0234; G05D 1/0236; G05D 1/0238; G05D 1/024; G05D 1/0242; G05D 1/0244; G05D 1/0246; G05D 1/0248; G05D 1/0251; G05D 1/0253; G05D 1/0094; G05D 1/00; G05D 1/0005; G05D 1/0011; G05D 1/0016; G05D 1/0027; G05D 1/0022; G05D 1/0033; G05D 1/0038; G05D 1/0044; G05D 1/005; G05D 1/0055; G05D 1/0061; G05D 1/0066; G05D 1/0072; G05D 1/0077; G05D 1/0083; G05D 1/0088;

G05D 1/0206; G05D 1/0204; G05D 1/0208; G05D 1/021; G05D 1/04; G05D 1/042; G05D 1/044; G05D 1/046; G05D 1/048; G05D 1/06; G05D 1/0607; G05D 1/0615; G05D 1/0623; G05D 1/063; G05D 1/0638; G05D 1/0646; G05D 1/0653; G05D 1/0661; G05D 1/0669; G05D 1/0676; G05D 1/0684; G05D 1/0688; G05D 1/0692; G05D 1/08; G05D 1/0808; G05D 1/0816; G05D 1/0825; G05D 1/0833; G05D 1/0841; G05D 1/085; G05D 1/0858; G05D 1/0866; G05D 1/0875; G05D 1/0891; G05D 1/10; G05D 1/101; G05D 1/102; G05D 1/104; G05D 1/106; G05D 1/1062; G05D 1/1064; G05D 1/107; G05D 1/108; G05D 1/12; G05D 1/22; G05D 1/221; G05D 1/222; G05D 1/223; G05D 1/2232; G05D 1/2234; G05D 1/2235; G05D 1/2242; G05D 1/224; G05D 1/2243; G05D 1/2244; G05D 1/2245; G05D 1/2246; G05D 1/2247; G05D 1/2248; G05D 1/2249; G05D 1/225; G05D 1/226; G05D 1/2265; G05D 1/227; G05D 1/2272; G05D 1/2274; G05D 1/2276; G05D 1/2278; G05D 1/2279; G05D 1/228; G05D 1/2285; G05D 1/2287; G05D 1/229; G05D 1/2295; G05D 1/2297; G05D 1/24; G05D 1/241; G05D 1/242; G05D 1/2424; G05D 1/2427; G05D 1/243; G05D 1/2435; G05D 1/2437; G05D 1/244; G05D 1/2446; G05D 1/2462; G05D 1/2464; G05D 1/2465; G05D 1/2467; G05D 1/2469; G05D 1/246; G05D 1/247; G05D 1/248; G05D 1/249; G05D 1/43; G05D 1/435; G05D 1/437; G05D 1/439; G05D 1/46; G05D 1/461; G05D 1/467; G05D 1/48; G05D 1/482; G05D 1/484; G05D 1/485; G05D 1/49; G05D 1/495; G05D 1/496; G05D 1/498; G05D 1/60; G05D 1/606; G05D 1/611; G05D 1/617; G05D 1/618; G05D 1/619; G05D 1/621; G05D 1/628; G05D 1/622; G05D 1/633; G05D 1/637; G05D 1/639; G05D 1/642; G05D 1/644; G05D 1/6445; G05D 1/645; G05D 1/646; G05D 1/6482; G05D 1/648; G05D 1/6484; G05D 1/6485; G05D 1/6486; G05D 1/65; G05D 1/651; G05D 1/652; G05D 1/654; G05D 1/6542; G05D 1/6545; G05D 1/6546; G05D 1/6548; G05D 1/656; G05D 1/661; G05D 1/663; G05D 1/665; G05D 1/667; G05D 1/672; G05D 1/678; G05D 1/683; G05D 1/686; G05D 1/689; G05D 1/6895; G05D 1/69; G05D 1/692; G05D 1/693; G05D 1/695; G05D 1/696; G05D 1/697; G05D 1/698; G05D 1/6983; G05D 1/6985; G05D 1/6987; G05D 1/80; G05D 1/81; G05D 1/815; G05D 1/817; G05D 1/82; G05D 1/83; G05D 1/85; G05D 1/852; G05D 1/854; G05D 1/857; G05D 1/86; G05D 1/87; G05D 1/0217; G05D 1/0212; G05D 1/0219; G05D 1/0221; G05D 1/0225; G05D 1/0223; G05D 1/0227; G05D 1/0229; G05D 1/0259; G05D 1/0255; G05D 1/0261; G05D 1/0263; G05D 1/0265; G05D 1/0268; G05D 1/027; G05D 1/0272; G05D 1/0274; G05D 1/0276; G05D 1/0278; G05D 1/028; G05D 1/0282; G05D 1/0285; G05D 1/0287; G05D 1/0289; G05D 1/0291; G05D 1/0293; G05D 1/0295; G05D 1/0297; G05D 1/03; G05D 1/105; G05D 1/20; G05D 1/245; G05D 1/40; G05D 1/02; G05D 2109/20; G05D 2109/22; G05D 2109/23; G05D 2109/24; G05D 2109/25; G05D 2109/254; G05D 2109/26; G05D 2109/265; G05D 2109/27; G05D 2109/285; G05D 2109/29; G05D 2111/00; G05D 2111/10; G05D 2111/14; G05D 2111/17; G05D 2111/30; G05D 2111/20; G05D 2111/32; G05D 2111/34; G05D 2111/36; G05D 2111/40; G05D 2111/50; G05D 2111/52; G05D 2111/54; G05D 2111/56; G05D 2111/58; G05D 2111/60; G05D 2111/63; G05D 2111/64; G05D 2111/65; G05D 2111/67; B60W 2420/408; B60W 60/001; B60W 60/00; B60W 60/0011; B60W 60/00256; B60W 60/005; B60W 60/0053; B60W 60/0051; B60W 60/0054; B60W 60/0055; B60W 60/0057; B60W 60/0059; B60W 60/0061; B60W 60/007; B60W 2556/50; B60W 30/06; G01S 13/862; G01S 13/867; G01S 13/865; G01S 13/86; G01S 13/74; G01S 13/87; G01S 13/872; G01S 13/88; G01S 13/887; G01S 13/56; G01S 13/00; G01S 13/04; G01S 13/50; G01S 13/06; G01S 2013/466; G01S 2013/468; G01S 13/52; G01S 13/66; G01S 13/90; G01S 13/9027; G01S 13/9021; G01S 2205/03; G01S 2205/00; G01S 5/00; G01S 13/726; G01S 13/72; G01S 13/68; G01S 13/685; G01S 13/70; G01S 13/723; G01S 13/885; G01S 2205/09; G01S 2205/10; B64U 2101/30; B64U 2101/31; B64U 2201/104; B64U 2201/10; B64U 2201/00; B64U 2101/64; B64U 2101/60; B64U 2101/69; B64U 2101/17; B64U 2101/55; B64U 2101/56; B64U 2101/57; B64U 2101/58; B64U 20/87; B64U 2101/00; B64U 2101/32; B64U 2101/67; G08G 5/0069; G08G 5/0052; G08G 5/0047; G08G 5/006; G08G 5/0056; G08G 5/0065; G08G 1/096725; G08G 1/096716; G08G 1/096708; G08G 5/0034; G08G 5/003; G08G 5/0039; G08G 5/0086; G08G 1/0968; G08G 1/096805; G08G 1/096811; G08G 1/096816; G08G 1/096822; G08G 1/096827; G08G 1/096833; G08G 1/096838; G08G 1/096844; G08G 1/09685; G08G 1/04; G08G 1/042; G08G 5/0021; G08G 5/065; G08G 5/025; G08G 5/854; G08G 5/02; G08G 5/04; G08G 5/045; G08G 5/06; B60R 25/25; B60R 25/252; B60R 25/255; B60R 25/257; B60R 2300/8093

See application file for complete search history.

(56) References Cited

U.S. PATENT DOCUMENTS

| | | |
|---|---|---|
| 7,555,383 B2 | 6/2009 | Siegel |
| 8,229,163 B2 | 7/2012 | Coleman et al. |
| 8,706,914 B2 | 4/2014 | Duchesneau |
| 8,780,195 B1 | 7/2014 | Rubin |
| 8,948,935 B1 | 2/2015 | Peeters et al. |
| 9,387,928 B1 | 7/2016 | Gentry et al. |
| 9,442,485 B1 | 9/2016 | McDermott et al. |
| 9,471,059 B1 | 10/2016 | Wilkins |
| 9,529,359 B1 | 12/2016 | Annan et al. |
| 9,607,219 B2 | 3/2017 | Greveson et al. |
| 9,645,582 B2 | 5/2017 | Shue |
| 9,874,308 B2 | 1/2018 | Saika et al. |
| 10,155,587 B1 | 12/2018 | Tang |
| 10,387,825 B1 | 8/2019 | Canavor et al. |
| 10,579,863 B2 | 3/2020 | Volkart |
| 2004/0030449 A1 | 2/2004 | Solomon |
| 2007/0112461 A1 | 5/2007 | Zini et al. |
| 2008/0043993 A1 | 2/2008 | Johnson |
| 2009/0076823 A1 | 3/2009 | Collins |
| 2009/0080715 A1 | 3/2009 | van Beek et al. |
| 2009/0216910 A1 | 8/2009 | Duchesneau |
| 2010/0034424 A1 | 2/2010 | Goossen |
| 2010/0299761 A1 | 11/2010 | Shapiro |
| 2011/0017863 A1 | 1/2011 | Goossen |
| 2011/0178658 A1 | 7/2011 | Kotabab et al. |
| 2012/0165976 A1 | 6/2012 | Cotner |
| 2013/0054010 A1 | 2/2013 | Holman et al. |
| 2013/0110281 A1 | 5/2013 | Jones et al. |
| 2013/0197718 A1 | 8/2013 | Lee et al. |
| 2013/0279668 A1 | 10/2013 | Rokosky et al. |
| 2014/0018979 A1 | 1/2014 | Goossen et al. |
| 2014/0140575 A1 | 5/2014 | Wolf |
| 2014/0152422 A1 | 6/2014 | Breed |
| 2014/0277691 A1 | 9/2014 | Jacobus et al. |
| 2015/0084774 A1 | 3/2015 | Wojcik et al. |
| 2015/0190925 A1 | 7/2015 | Hoffman et al. |
| 2015/0215254 A1 | 7/2015 | Bennett |
| 2015/0360365 A1 | 12/2015 | Fudaba et al. |
| 2016/0063987 A1 | 3/2016 | Xu et al. |
| 2016/0116912 A1* | 4/2016 | Nehmadi ............. G05D 1/0022 701/2 |
| 2016/0173827 A1 | 6/2016 | Dannan et al. |
| 2016/0225048 A1 | 8/2016 | Zoldi et al. |
| 2016/0236790 A1 | 8/2016 | Knapp et al. |
| 2016/0253889 A1 | 9/2016 | Keyton |
| 2016/0288905 A1 | 10/2016 | Gong et al. |
| 2017/0053169 A1 | 2/2017 | Cuban |
| 2017/0092109 A1 | 3/2017 | Trundle et al. |
| 2017/0126691 A1 | 5/2017 | Arcese et al. |
| 2017/0147976 A1 | 5/2017 | Koch et al. |
| 2017/0161725 A1 | 6/2017 | Hosp et al. |
| 2017/0177925 A1 | 6/2017 | Volkart |
| 2017/0225336 A1 | 8/2017 | Deyle et al. |
| 2020/0279100 A1 | 9/2020 | Volkart |

OTHER PUBLICATIONS

International Search Report and Written Opinion directed to related International Patent Application No. PCT/US2018/028354, dated Jul. 9, 2018; 16 pages.

International Search Report and Written Opinion directed to related International Patent Application No. PCT/US2018/027146, dated Jun. 28, 2018; 8 pages.

Hsu et al., Face Recognition on Drones: Issues and Limitations, May 18, 2015 (retrieved Apr. 5, 2019), DroNet '15 Proceedings of the First Workshop on Micro Aerial Vehicle Networks, Systems, and Applications for Civilian Use, pp. 39-44. Retrieved: https://dl.acm.org/citation.cfm?id=2750679 (Year: 2015).

Boyers. An Evaluation of Detection and Recognition Algorithms to Implement Autonomous Target Tracking With a Quadrotor, Nov. 2013 (retrieved Apr. 5, 2019), Thesis, 97 total pages. Retrieved: http://www.cs.ru.ac.za/research/g10b3981/Thesis.pdf (Year: 2013).

Specification of U.S. Appl. No. 62/235,045, filed Sep. 30, 2015 corresponding to US Patent App. Pub. No. US 2017/0092109 to Trundle et al. (Year: 2015).

Specification of U.S. Appl. No. 62/167,241, filed May 27, 2015 corresponding to U.S. Pat. No. 9,874,308 to Saika et al. (Year: 2015).

Foo et al., Path Planning of Unmanned Aerial Vehicles using B-Splines and Particle Swarm Optimization, Apr. 2009, May 23, 2012: Online [retrieved May 18, 2023], Journal of Aerospace Computing, Information, and Communication, vol. 6, pp. 271-290. Retrieved: https://arc.aiaa.org/doi/abs/10.2514/1.36917 (Year: 2009).

Hrabar et al., Combined Optic-Flow and Stereo-Based Navigation of Urban Canyons for a UAV, Aug. 2-6, 2005 [retrieved May 18, 2023], 2005 IEEE/RSJ International Conference on Intelligent Robots and Systems, 8 pages. Retrieved: https://ieeexplore.ieee.org/abstract/document/1544998 (Year: 2005).

U.S. Appl. No. 62/262,895, Emergency response system using unmanned aerial vehicle (UAV), of Tang (U.S. Pat. No. 10,155,587), Dec. 3, 2015 [retrieved Apr. 4, 2022], 18 pages. (Year: 2015).

Drawings of U.S. Appl. No. 62/262,895, Emergency response system using unmanned aerial vehicle (UAV), of Tang (U.S. Pat. No. 10,155,587), Dec. 3, 2015 [retrieved Apr. 4, 2022], 7 pages. (Year: 2015).

* cited by examiner

UNMANNED AERIAL VEHICLE WITH BIOMETRIC VERIFICATION

CROSS-REFERENCE TO RELATED APPLICATIONS

This application is a continuation of U.S. Nonprovisional patent application Ser. No. 16/807,634, filed on Mar. 3, 2020, which is a continuation of U.S. Nonprovisional patent application Ser. No. 14/971,891, filed on Dec. 16, 2015, issued as U.S. Pat. No. 10,579,863 titled "Unmanned Aerial Vehicle With Biometric Verification," and the contents of which are hereby incorporated herein by reference in their entireties.

FIELD OF THE INVENTION

The present invention relates generally to the field of unmanned aerial vehicle systems used in law enforcement, penal institutions, or similar facilities. In particular, the present invention relates to an unmanned aerial vehicle in communication with a computer-based system with the capacity to capture, record, monitor, and identify biometric features of a persons of interest.

BACKGROUND OF THE PRESENT INVENTION

In the 1993 film "The Fugitive", actor Tommy Lee Jones famously related the following quote: "[o]ur fugitive has been on the run for 90 minutes. Average foot speed over uneven ground, barring injuries, is 4 miles-an-hour. That gives us a radius of six miles. What I want out of each and every one of you is a hard-target search of every gas station, residence, warehouse, farmhouse, henhouse, outhouse and doghouse in that area.

Checkpoints go up at fifteen miles." Whether the data quoted by Mr. Jones is accurate or not, it is generally well known that in the event of a prison escape, a robbery, a child abduction, a person reported missing, etc., time is very critical. The more time a person has to get away, the larger the search area becomes. As the search area grows, the price and cost of the search increases exponentially.

During the summer of 2015, two men escaped from an upstate New York Prison. Initially, search dogs, helicopters, and hundreds of police officer and corrections officers searched the wilderness and local communities, going house to house in neighborhoods. Two days after the fugitives escaped, the State of New York offered a $100,000 reward for information that lead to the fugitives capture. One week into the search, the 16-square-mile search area produced no results. It is reported that over 1,000 police officers, Federal Bureau of Investigation (FBI) agents, and United States Marshalls assisted in the 23-day search. It is further reported that the manhunt cost the state approximately $23 million dollars.

SUMMARY OF INVENTION

The present disclosure provides an improved subject monitoring system, comprising an unmanned aerial vehicle equipped with a global positioning system receiver capable of determining the location of the unmanned aerial vehicle, a microphone capable of capturing a voice sample associated with a monitored subject (or person), and a communications port capable of transmitting and receiving electronic data over a communications medium. The subject monitoring system further includes a computing system that can transmit and receive data to/from the unmanned aerial vehicle. As described herein, the computing system has a user interface, a processor, and a number of modules implemented to control and perform various functionalities. For example, a steering module may be used. The steering module may be configured to control the movements of the unmanned aerial vehicle based on electronic data received at the user interface. In an embodiment, a voice analysis module is used to authenticate the identity of the monitored subject.

It is a further object of this disclosure to deploy an unmanned aerial vehicle, operate the UAV in accordance with the mode of operation of the UAV, determine whether a subject has been detected, capture a first voice sample associated with the subject, authenticate the identity of the subject, and transmit the GPS location of the unmanned aerial vehicle to a computing device.

The main objective of the present disclosure is to provide a UAV with the capabilities of locating, identifying, and tracking a known criminal, fugitive, missing person, and/or any other person of interest, as well as providing general law enforcement support functions.

BRIEF DESCRIPTION OF THE DRAWINGS

A further understanding of the present disclosure can be obtained by reference to the preferred embodiment and alternate embodiments set forth in the illustrations of the accompanying drawings. Although the illustrated embodiments are merely exemplary of systems for carrying out the present invention, both the organization and method of operation of the invention, in general, together with further objectives and advantages thereof, may be more easily understood by reference to the drawings and the following description. The drawings are not intended to limit the scope of this disclosure, which is set forth with particularity in the claims as appended or as subsequently amended, but merely to clarify and exemplify the invention. For a more complete understanding of the present disclosure, reference is now made to the following drawings in which:

In the drawings, like reference numbers generally indicate identical or similar elements. Additionally, generally, the left-most digit(s) of a reference number identifies the drawing in which the reference number first appears.

DETAILED DESCRIPTION OF THE INVENTION

As required, a detailed illustrative embodiment of the present invention is disclosed herein. However, techniques, systems and operating structures in accordance with the present disclosure may be embodied in a wide variety of forms and modes, some of which may be quite different from those in the disclosed embodiment. Consequently, the specific structural and functional details disclosed herein are merely representative, yet in that regard, they are deemed to afford the best embodiment for purposes of disclosure and to provide a basis for the claims herein, which define the scope of the present invention. The following presents a detailed description of a preferred embodiment as well as alternate embodiments such as a simpler embodiment or more complex embodiments for alternate devices of the present invention.

An unmanned aerial vehicle (UAV) is an aircraft that may be manually controlled at a remote location or can fly autonomously based on programmed flight. Currently, UAV's cannot verify or authenticate the identity of a monitored subject such as a known criminal, fugitive, missing person, and/or any other person of interest.

In view of the foregoing, there exists a need for an improved method and apparatus for locating, identifying, and tracking a known criminal, fugitive, missing person, and/or any other person of interest.

Figure 1:
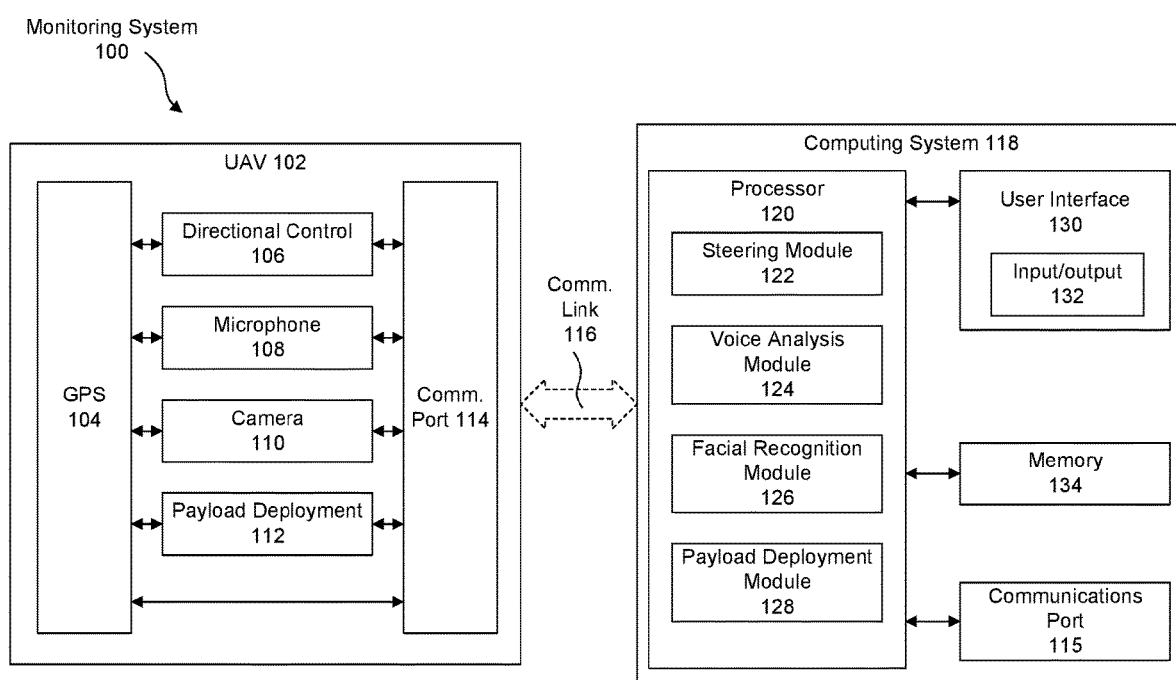
FIG. 1 depicts a functional block diagram of an exemplary monitoring system.

FIG. 1 illustrates a functional block diagram of an exemplary monitoring system 100, useful for implementing various embodiments of the present disclosure. As depicted, an unmanned aerial vehicle ("UAV") 102 is in electronic communication with at least one computing system 118 over communications link 116. In an embodiment, the UAV 102 includes one or more features to provide additional functionality. For example, the UAV 102 may include, for example, global positioning system ("GPS") receiver 104, directional control system 106, microphone 108, camera 110, payload deployment system/mechanism 112, and communications port 114. The computing system 118 likewise includes one or more features to provide additional functionality. For example, computing system 118 may include at least one processor 120, user interface 130, and memory 134. In an embodiment, the processor(s) may additionally include steering module 122, voice analysis module 124, facial recognition module 126, and payload deployment module 128. In an embodiment, user interface 130 may further include user input/output device(s) 132.

For purposes of this discussion, the term "module" shall be understood to include at least one of software, firmware, and hardware (such as one or more circuit, microchip, processor, or device, or any combination thereof), and any combination thereof. In addition, it will be understood that each module may include one, or more than one, component within an actual device, and each component that forms a part of the described module may function either cooperatively or independently of any other component forming a part of the module. Conversely, multiple modules described herein may represent a single component within an actual device. Further, components within a module may be in a single device or distributed among multiple devices in a wired or wireless manner. As such, one or more modules may be used alone (or in combination) to provide an improved systems and methods for locating, identifying, authenticating, and/or tracking the location and movements of a law enforcement officer, search and rescue team member, a known criminal, fugitive, missing person, and/or any other person of interest.

UAV 102 is an unmanned aircraft that can fly autonomously, i.e., on auto-pilot, based on a pre-programmed flight pattern and/or that can be controlled by a remote operator/pilot. In an embodiment, the UAV is flown semi-autonomously. In an embodiment, the UAV may be implemented as a helicopter having at least one rotor to lift and propel the aircraft, each rotor having a plurality of blades; a quadcopter, having four rotors to lift and propel the aircraft; or any other type of unmanned flying machine capable of performing the methods described herein.

In an embodiment, the UAV includes GPS receiver 104. GPS receiver 104 may be implemented using either global navigation satellite system (GNSS) type receivers or any other GPS receiver capable of providing the UAV's real-time location.

In an embodiment, UAV 102 further includes directional control system 106. Directional control system 106 can be implanted as circuitry, a microprocessor, a processor, or any other means that can convert data signals into an electronic signals that cause components of the UAV to lift, propel and steer the UAV. In an embodiment, direction control system sends and receives data with GPS receiver 104 in order to direct, i.e., fly, the UAV to either a desired or pre-programmed location. Further, the direction control system sends and receives data with communications port 114. As will be discussed in greater detail below, a remote operator (or pilot) sends movement commands to the UAV through communications port 114. Communications port 114 provides the commands to the directional control system in order to fly the UAV to a desired location.

In an embodiment UAV 102 further includes microphone 108. The microphone 108 can be any of one or more of traditional microphones, a parabolic microphone, a laser Doppler vibrometer (LDV), or any other microphone or combination of microphones capable of capturing voice signals. In an embodiment, microphone 108 further includes a cone, a parabolic dish, or is placed about a gimbal or a piezoelectric motor system. In such embodiments the gimbal (and/or piezoelectric motor system) is programmed to point the microphone toward a desired subject. Alternatively, the gimbal (and/or piezoelectric motor system) is be controlled remotely by an operator (or pilot) through a communications port (such as communications port 114 of FIG. 1).

The microphone further includes an internal/embedded digital signal processor (DSP). The DSP may be programmed to perform audio signal analysis, to automatically adjust gain control, to compensate for variations in the level of incoming audio signals, to compress digitized voice data compression, to send and/or receive dual tone multi frequency signals (DTMF) or in-band signaling, to monitor channel conditions and status, to detect presence of tones, and to detect silence/quiet.

In an embodiment UAV 102 further includes camera 110. The camera 110 may be a digital camera capable of capturing facial images of a subject. The camera must provide images with a high enough quality, or definition, in order to perform facial recognition tasks. In an embodiment, the camera provides still digital images. In alternative embodiments, the camera provides video. In yet additional embodiments, the camera provides a real-time video feed to an operator (or pilot) through a communications port 114. The camera may be secured to a gimbal and/or a piezoelectric motor system. In such embodiments the gimbal (and/or piezoelectric motor system) may be programmed to point the camera toward a desired subject in order to capture a facial image of the subject. Alternatively, the gimbal (and/or piezoelectric motor system) may be controlled remotely by an operator (or pilot) through the communications port. As shown, the camera additionally exchanges data with GPS receiver 104. In such embodiments the captured images further include metadata related to the GPS location of the photographed (or filmed) subject and/or the GPS location of the UAV while the images were captured.

In an embodiment, the camera may additionally comprises thermo-graphic, infrared, night-vision, and/or thermal imaging capabilities in order to identify and/or authenticate the identity of an individual, such as a law enforcement officer, a known criminal, fugitive, missing person, and/or any other person of interest.

In an embodiment, the camera may additionally comprise magnification capabilities, where the camera can automatically (or manually) zoom-in or zoom-out in order to obtain images of a person to identify and/or authenticate the identity of an individual in the captured image.

In an embodiment, the camera further includes an image processor. The image processor may be programmed to perform image analysis, to automatically adjust brightness, saturation, contrast, or other image features, to compensate for variations in lighting, definition, pixilation, etc. of varying between captured images, to compress image/video files, to frame identifying features within an image/video, to decompress stored image data, to compress image, video, and/or live feed data for playback, to adjust the rate/speed of video playback.

In an embodiment, UAV 102 further includes payload deployment system/mechanism 112. Payload deployment system/mechanism 112 may include circuitry, a microprocessor, processor or any other means capable of controlling the deployment of a payload. In an embodiment where the payload is a pressurized gas (such as pepper spray or tear gas), the payload deployment system/mechanism includes a cavity designed to receive a pressurized gas canister, including any required mechanism for controlling the release of the pressurized gas. In an embodiment where the payload is a projectile (such as rubber bullets, bean-bags, or other non-lethal ammunition) the payload delivery system includes a suitable gun, firearm, or launcher to project the ammunition toward a desired location. In an embodiment where the payload is a deployable canister (such as tear gas, a flash canister, or pepper spray), the payload delivery system may include releasable hooks, a releasable door, a sliding door, or any other means capable of releasing and/or activating the payload. In embodiments where the payload is an aid kit, food, water, firearms, rope, or any other supply that may be needed, the payload delivery system may include releasable hooks, a releasable door, a sliding door, or any other means capable of releasing the payload.

In an embodiment, the payload deployment system/mechanism (such as payload deployment system/mechanism 112 of FIG. 1) is pre-programmed to activate upon the occurrence of an event, when the UAV has reached a desired location, when the identity of a subject has been authenticated, or at the occurrence of any other foreseeable event commonly encountered while chasing a known criminal, a fugitive, or when rescuing someone in need. Further, the payload deployment system/mechanism may be activated by an operator (or pilot) by sending a command to the payload deployment system/mechanism through a communications port (such as communications port 114 of FIG. 1).

In an embodiment, the UAV further includes a speaker and/or flashing lights. In such embodiments, the speaker may be used to allow an operator (or pilot) to communicate with the monitored subject. Further, the microphone may be used to attempt to bait, or entice, the monitored subject to speak, so a voice signal sample may be collected. Further, the speaker and/or flashing lights may be used to catch the attention of the monitored subject in order to bait, or entice, the monitored subject to look at the camera, so a facial image may be collected.

In an embodiment, the UAV is equipped with a noise cancellation system to cancel, attenuate, or eliminate any noise created by the operation of the UAV and/or the UAV propellers.

As depicted in FIG. 1, UAV 102 is electronically coupled to computer system 118 through communications link 116. In an embodiment, communications port 114 of UAV 102 sends/receives data across communications link 116 to/from communications port 115 of computer system 118. A communications link (such as communications link 116 of FIG. 1) may be implemented using at least one mobile or wireless communications protocol, such as: long term evolution (LTE), Wi-Fi, Bluetooth, radio-frequency, first generation (1G) wireless technology, second generation (2G) wireless technology, third generation (3G) wireless technology, fourth generation (4G) wireless technology, code-division multiple access (CDMA), frequency division multiple access (FDMA), generic access network (GAN), global system for mobile (GSM), or any other wireless protocol capable of creating a communications link between a UAV and at least one computer system. In an embodiment, the communications link is implemented using a wired connection. In such embodiments, at least one computing system may be located onboard the UAV. In an alternative embodiment, the UAV may be tethered to at least one computing system using a cable, wire, or other means for passing data through a wired connection. Various example, non-limiting embodiments, of contemplated monitoring system configurations shall now be discussed.

As depicted in FIG. 1, computing system 118 is implemented on a single device. As mentioned above, the computing system may include one of more features to provide additional functionality. In an embodiment, the computing system may further include input/output device(s) 132, such as monitors, keyboards, pointing devices, joysticks, throttles, buttons, wheels, touchscreens, graphical user interface buttons (GUI), etc., that communicate with a processor through user interface 130.

A user interface (such as user interface 130 of FIG. 1) and applicable input/output devices (such as input/output device (s) 132 of FIG. 1) may be used to manually control various functional features of a monitoring system. For example, in an embodiment, a joystick is used to control the direction, location, and/or movement of the UAV (such as UAV 102 of FIG. 1). In an embodiment, a monitor is used to view images, video, or watch a live feed provided by a UAV. In an additional embodiment, a touchscreen is used to display authentication results provided by a processor.

In an embodiment, computing system 118 further includes memory 134. Memory 134 is implemented as a main or primary memory, such as random access memory (RAM). Memory 134 may include one or more levels of cache. The memory may have stored therein control logic, such as computer software, and/or data. In additional embodiments, memory may also include one or more secondary storage devices or memory such as a hard disk drive and/or a removable storage device or drive. The removable storage drive may include a floppy disk drive, a magnetic tape drive, a compact disk drive, and/or any other storage device/drive.

In an embodiment, the computing system further includes at least one processor. As depicted in FIG. 1, processor 120 further includes steering module 122, voice analysis module 124, facial recognition module 126, payload deployment module 128, and/or any other module necessary to perform the functionality described herein. In additional embodiments processor 120 includes only a single module or any modules contemplated herein. Each module may be implemented as logic embodied in software, firmware, hardware, and/or operating system implementations in order to perform or carry-out a desired function. Further, as used herein, a module may also be implemented a collection of software instructions. One or more software instructions in the modules may be embedded in firmware, such as in an erasable programmable read only memory (EPROM). The modules described herein may also be stored in any type of non-transitory computer-readable medium or other storage device.

Figure 2A:
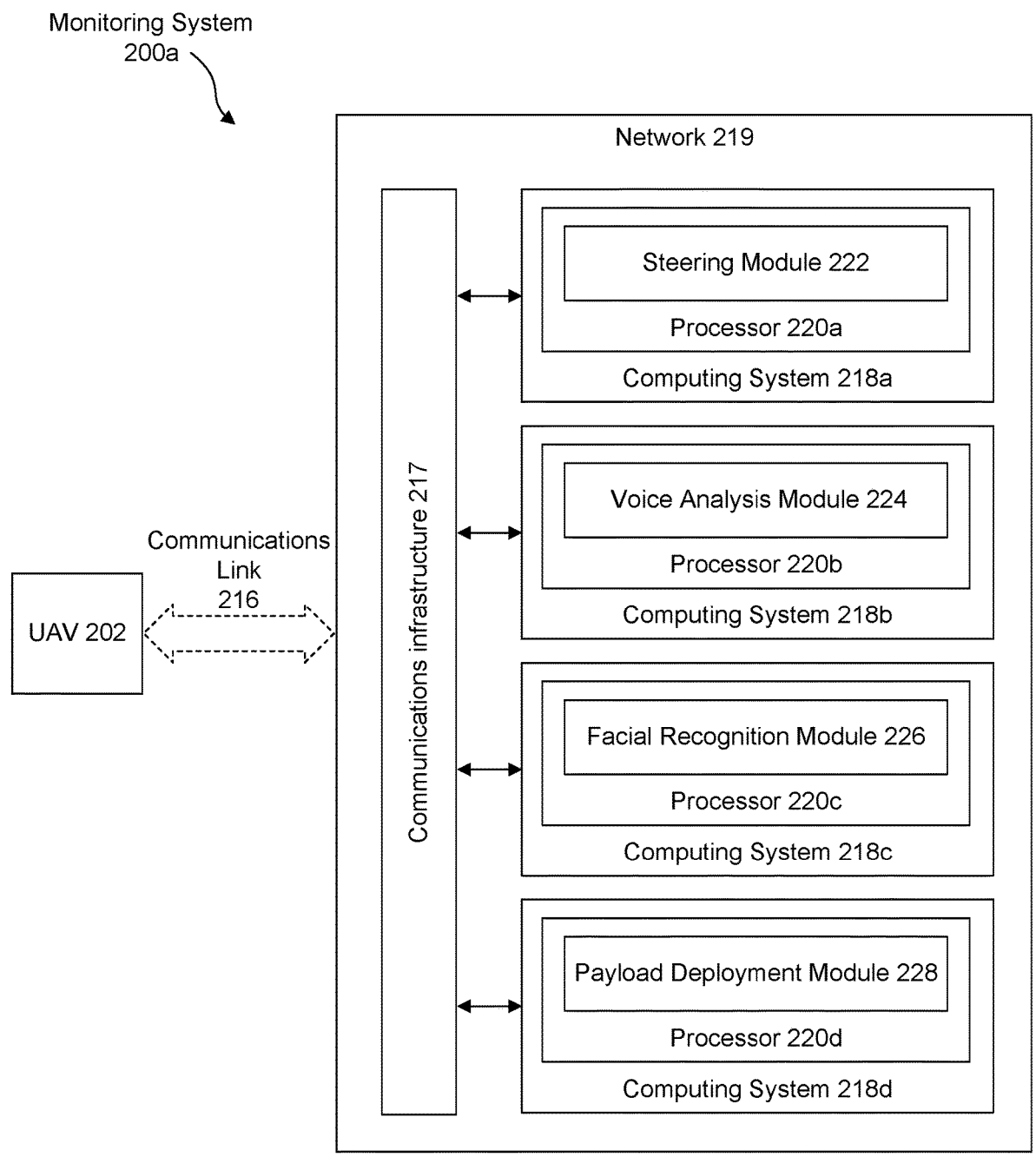
FIGS. 2A-2B depict functional block diagrams of exemplary monitoring systems.

In an embodiment, the modules are incorporated using a single computing system and processor. In other embodiments, the modules are incorporated using more than one computing system and/or processor. Referring now to FIG. 2A, shown is non-limiting functional block diagram of monitoring system 200a, useful for implementing various embodiments of the present disclosure. As shown, UAV 202 is in electronic communication with network 219 through communications link 216. Network 219 may be comprised of computer systems 218a-d, each having at least one processor 220a-d, respectively. The processors 220a-d may send and receive data to other processors within the network and/or the UAV through communications infrastructure 217. For example, in an embodiment, facial recognition module 226, located within computing system 218c and processor 220c, communicates with UAV 202 by transmitting data through communications infrastructure 217 and communications link 216. In another non-limiting example, voice analysis module 224 located within computing system 218b and processor 220b, sends and receives data with steering module 222 through communications infrastructure 217.

A network (such as network 219 of FIG. 2A) may be implemented as a wide area network (WAN), a local area network (LAN), a metropolitan area network (MAN), or any other network capable of performing the functionality described herein. As such, a communications infrastructure (such as communications infrastructure 217 of FIG. 2A) may be a wired and/or wireless connection. Further, the communications infrastructure may operate using a communications protocol such as: long term evolution (LTE), Wi-Fi, Bluetooth, radio-frequency, first generation (1G) wireless technology, second generation (2G) wireless technology, third generation (3G) wireless technology, fourth generation (4G) wireless technology, code-division multiple access (CDMA), frequency division multiple access (FDMA), generic access network (GAN), global system for mobile (GSM), or any other network protocol capable of sending and receiving data between nodes within a network and/or a UAV.

Figure 2B:
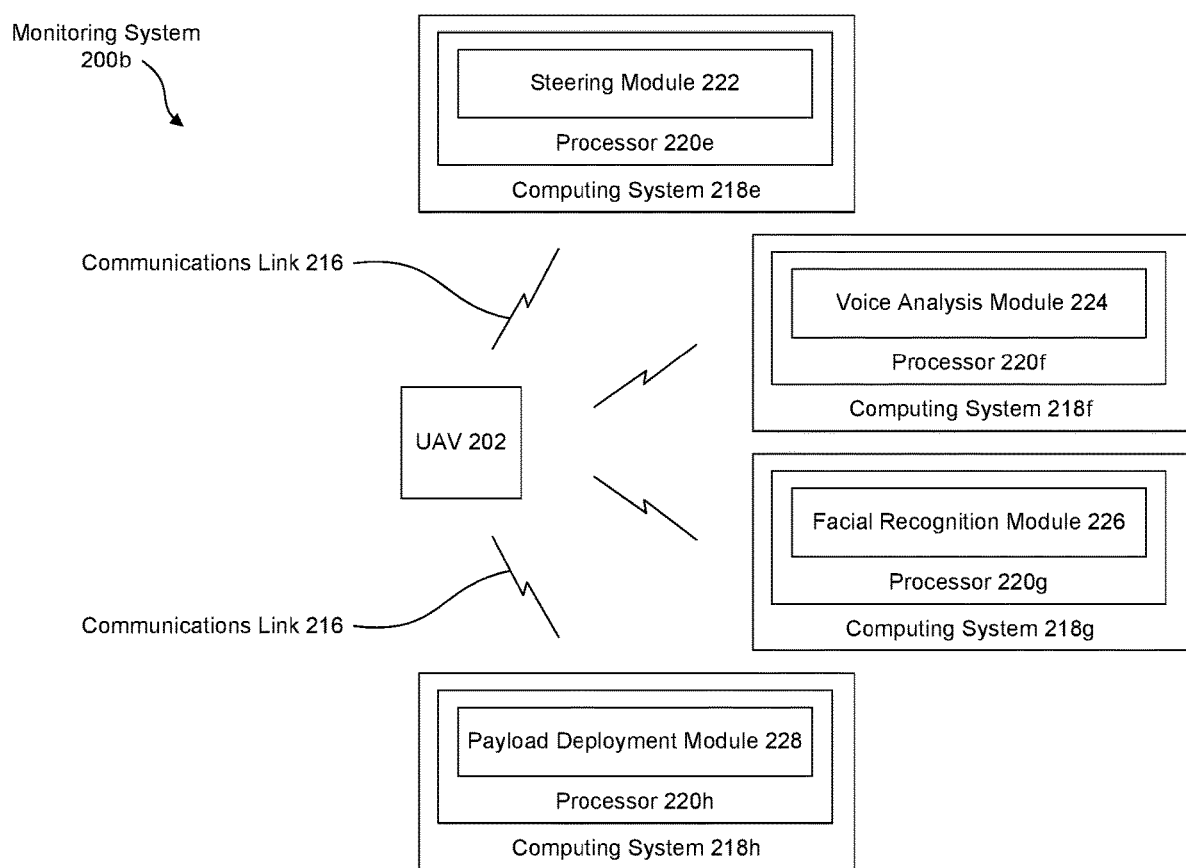

Referring now to FIG. 2B, shown is non-limiting functional block diagram of monitoring system 200b, useful for implementing various embodiments of the present disclosure. As shown, UAV 202 is in electronic communication with multiple computing systems 218e-h over communications link 216, each computing system having at least one processor 220e-h therein.

As depicted in FIG. 2B, each processor 220e-h contains one module therein. In other embodiments, however, a processor 120 may comprise multiple modules. For example, a monitoring system may be implemented using one computing system having multiple processors, each processor having at least one module therein. For example, in an embodiment where the monitoring system (such as monitoring system 100 of FIG. 1) only requires a steering module and a voice analysis module, the steering module may be implemented using a first computing system while the voice analysis module may be implemented using a second computing system. In another non-limiting embodiment, where the monitoring system only requires a steering module, a facial recognition module, and a payload deployment, the steering module and payload deployment module are implemented using a first computing system or processor while the facial recognition module is implemented using a second computing system or processor. In an embodiment, where only one module is necessary, that module may be implemented using a plurality of computing systems or processors, each acting as a node within a network.

Various example, non-limiting embodiments, of contemplated software, firmware, hardware, and/or operating system modules shall now be discussed.

A steering module (such as steering module 122 of FIG. 1 or steering module 222 of FIGS. 2A and 2B) may provide directional commands to a UAV. The steering module may perform directional commands, including: providing the UAV with real-time route and GPS coordinates, analyzing a map and providing the UAV with a desired auto-pilot travel route, and/or analyzing geographic features of the area and providing instructions to ensure the UAV avoids any nearby obstacles. In an embodiment, the steering module performs directional commands in response to operator (or pilot) instructions received from input/output devices 132 through a user interface. The steering module may perform the directional commands using software, firmware, hardware, and/or operating system implementations.

Voice analysis module 124 and/or voice analysis module 224 may be implemented to compare voice signals against stored voiceprints in order to identify and/or authenticate the identity of a subject, such as a criminal, fugitive, missing person, and/or any other person of interest. Further, the voice analysis module may code captured voice signals into digitized voice files (or voiceprints) for recording and use for authentication. The voice analysis module may also decode user digitized voice files and convert the digital signals to audio signals for playback. In an embodiment, the voice analysis module receives a voice signal captured using a UAV, converts the capture voice signals into a digitized voice file, and compares the digitized voice signal against voiceprints stored in a voiceprint database in order to identify a criminal, fugitive, missing person, and/or any other person of interest. In an embodiment, the voiceprint database comprises at least one voice signal sample of a subject along with the subject's identifying information.

Voice analysis module 124 and/or voice analysis module 224 further includes an internal/embedded digital signal processor (DSP). The DSP may be programmed to perform audio signal analysis, to automatically adjust gain control, to compensate for variations in the level of incoming audio signals, to compress digitized voice data compression, to send and/or receive dual tone multi frequency signals (DTMF) or in-band signaling, to monitor channel conditions and status, to detect presence of tones, detect silence/quiet, to decompress stored audio data, to compress audio data for playback, to adjust the volume and rate of speed of playback, in order to identify and/or authenticate the voice of a criminal, fugitive, missing person, and/or any other person of interest.

In an embodiment, the voiceprint database comprises voice signal samples provided willingly by any subject, i.e., person, at any time. In an additional embodiment, the voice signal sample may be provided by a family member of the subject. For example, in an embodiment where monitoring system 100 or monitoring systems 200a and 200b is used to locate and identify a missing person, voice signal samples of the missing person may be provided by friends and/or family members. In an embodiment, the voiceprint database may comprise voice signal samples provided by an inmate, a convicted criminal, or other family members during registration and/or any other time in order to identify and/or authenticate the voiceprint of a criminal, fugitive, missing person, and/or any other person of interest. A national voice database may also be used to access voice signal samples of wanted criminals.

Upon storing a voice signal sample in the voiceprint database, the voice analysis module analyzes a characteristic of the voice signal data such as, in one non-limiting example, the pitch (i.e., tonal quality) over a period of time. However, in other non-limiting examples, the voice analysis module may analyze duration, loudness, stress, emotion, mixed-frequencies, timbre, or other similar types of characteristics in the voice data, or a combination of these characteristics. Based on an analysis of these characteristics, the system generates a voiceprint—a unique biometric measurement of the person's voice—that can be compared to other voiceprints to determine a statistical "match" for identifying a person such as criminal, fugitive, missing person, and/or any other person of interest. In one example, the voice data of the speaker would be measured and recorded after, for as few as 3-5 seconds.

Calculated voiceprints are stored in the voiceprint database. In an embodiment, to obtain a baseline pitch with which to compare, a subject might be required to read a script for a period of time during registration or other time so an average value of pitch could be established for future use. In an embodiment the voice sample files may be stored in format where a user may replay the sample. In other embodiments, only the extracted pitch, tonal quality, loudness, timbre, etc., may be stored as a voiceprint.

Digital voice sample files and/or voiceprint database may be stored in memory 134. In another embodiment, however, the digital voice sample files and/or voiceprint database are stored anywhere accessible to the monitoring system, whether local or remote. The voice analysis module may perform its operations using software, firmware, hardware, and/or operating system implementations.

Facial recognition module 126 and/or facial recognition module 226 are implemented to compare an image of a subject's face, i.e., facial image, against stored images and/or faceprint data in order to identify and/or authenticate the identity of a subject such as a criminal, fugitive, missing person, and/or any other person of interest. In an embodiment, the facial recognition module receives an image, video, or live feed captured using a UAV and compare the received image, video, or live feed against facial images stored in an image database. In an embodiment, the image database comprises at least one facial image of a subject along with the subject's identifying information. For example, the image database In an embodiment, the facial recognition module further includes an image processor. The image processor may be programmed to perform image analysis, to automatically adjust brightness, saturation, contrast, or other image features, to compensate for variations in lighting, definition, pixilation, etc. of varying between captured images, to compress image/video files, to frame identifying features within an image/video, to decompress stored image data, to compress image, video, and/or live feed data for playback, and to adjust the rate/speed of video playback in order identify and/or authenticate the facial image of a criminal, fugitive, missing person, and/or any other person of interest.

In an embodiment, the image database comprises sample images taken of, or provided by, any subject at any time. In an embodiment, the image sample may be provided by the family member of a subject. For example, in an embodiment where the monitoring system 100 or monitoring systems 200a and 200b are used to locate and identify a missing person, image samples of the missing person may be provided by friends and/or family members. In an embodiment, the image database may comprise image samples taken of an inmate, a convicted criminal, or other family members during registration and/or any other time. A national image database may also be used to access image samples of wanted criminals.

Upon storing an image sample in the image database, the facial recognition module may analyze at least characteristic of the image data. For example, the facial recognition module may identify facial features by extracting landmarks, or features, from an image of the subject's face to create a faceprint. For example, the facial recognition module may analyze the relative position, size, and/or shape of the eyes, nose, cheekbones, and jaw. In another embodiment, the facial recognition module may normalize and compress the facial image data, only saving the data in the image that is useful for face recognition. In such embodiments, an image provided by the UAV may then then compared with the stored facial data in order to identify and/or authenticate the facial image of a criminal, fugitive, missing person, and/or any other person of interest.

The facial recognition module may be implemented as: a geometric system, which looks at distinguishing features; as a photometric system, which is a statistical approach that distills an image into values and compares the values with templates to eliminate variances; as a 3-dimensional system, which uses 3D sensors to capture information about the shape of a face, including distinctive features on the surface of a face, such as the contour of the eye sockets, nose, and chin; or as a skin texture system, which turns the unique lines, patterns, and spots apparent in a person's skin into a mathematical space. Further, the facial recognition module employs any combination of these implementations.

Image/video files and/or image database may be stored in memory (such as memory 134 of FIG. 1). In another embodiment, however, the image sample files and/or image database may be stored anywhere accessible to the monitoring system (such as monitoring system 100 of FIG. 1 or monitoring systems 200a and 200b of FIGS. 2A and 2B, respectively), whether local or remote. The facial recognition module may perform its operations using software, firmware, hardware, and/or operating system implementations.

Payload deployment module 128 and/or payload deployment module 228 provides payload deployment commands to the UAV. The payload deployment module may perform commands, including: providing the UAV with real-time payload deployment commands, providing the UAV with pre-programmed payload deployment commands, and/or providing the UAV with situational payload deployment commands based on the occurrence of an event. The steering module may perform payload deployment commands in response to operator (or pilot) instructions received from input/output devices (such as input/output devices 132 of FIG. 1). The payload deployment module may perform the payload deployment commands using software, firmware, hardware, and/or operating system implementations.

Various example, non-limiting embodiments, of contemplated monitoring system methods shall now be discussed.

Figure 3:
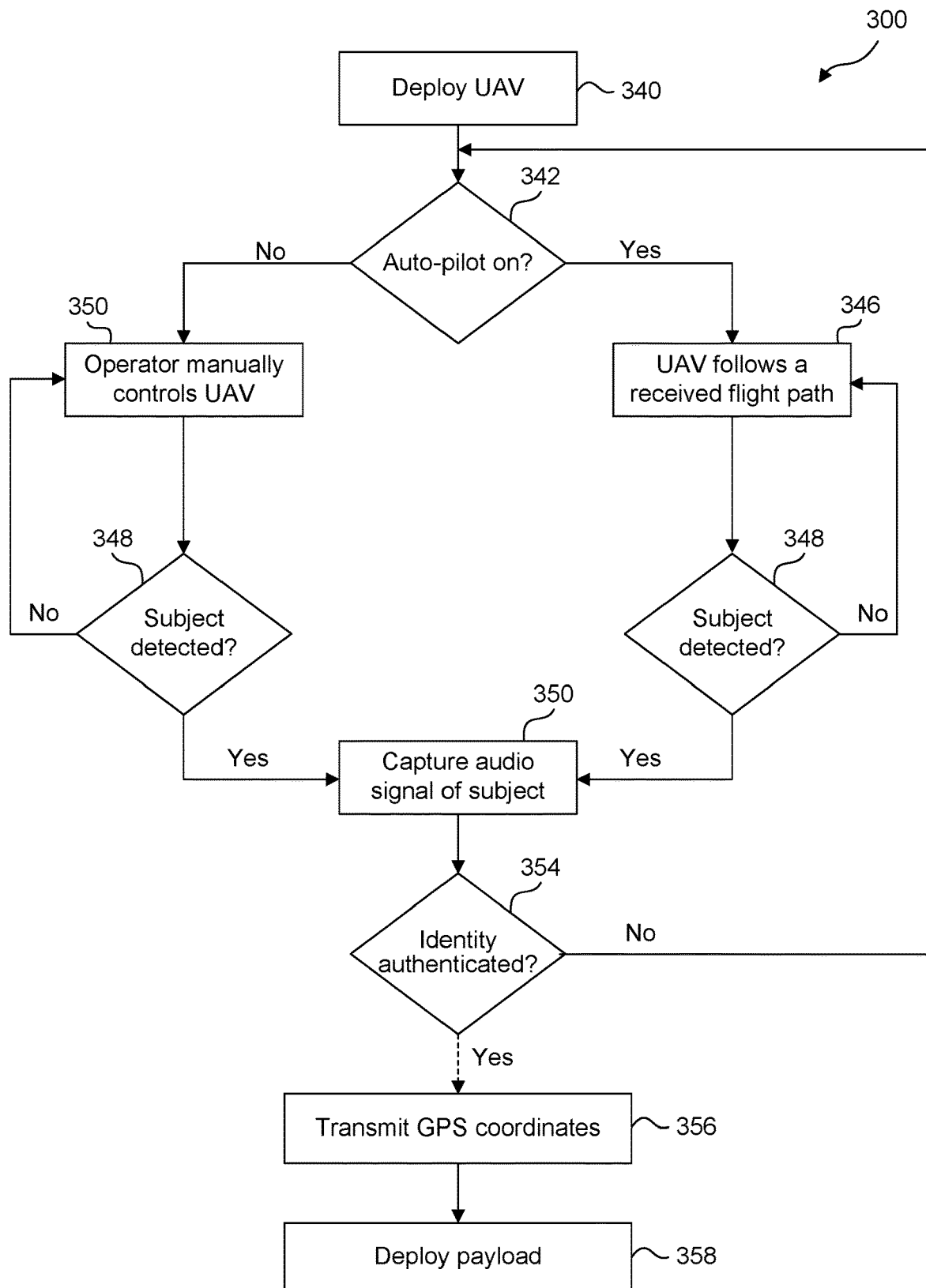
FIG. 3 depicts a flow chart diagram of an exemplary method for locating a person of interest, using a UAV.

FIG. 3 illustrates method 300, a method for locating a person of interest, using a UAV. At step 340, the UAV is deployed. The UAV may be deployed by launching the UAV and/or preparing to launch the UAV.

At step 342, it is determined whether the UAV is in auto-pilot mode or whether it is in manual operation mode. If the UAV is in auto-pilot mode, at step 346, the UAV follows a received pre-programmed auto-pilot flight path. As mentioned above, the auto-pilot flight path may include geographic obstacles that the UAV must negotiate around. Additionally, the auto-pilot flight path may include a "swath" path, where the UAV will fly in pre-determined lines in order to fly over a specific plot of land. At any time, an operator may interrupt the auto-pilot flight and begin operating the UAV in manual operation mode (not illustrated in FIG. 3). For example, when the UAV is flying in auto-pilot mode and an operator would like to observe something from a different distance, angle, or for a longer period of time, he or she may take control of the UAV. In an embodiment, the pilot may press a button or sequence of buttons to initialize a new pre-programmed flight maneuver. Further, the operator (or pilot) may modify the programmed flight path at any time during operation. At any time, the operator may return the UAV to auto-pilot mode and the UAV returns to the GPS location where the operator interruption took place and resume the predetermined flight path.

Now returning to step 342. If at step 342, the UAV has been deployed in manual operation mode, the operator controls of the UAV. At step 350, the operator (or pilot) controls the movements of the UAV using input/output devices (such as input/output device(s) 132 of FIG. 1) through a user interface (such as user interface 130 of FIG. 1). In an embodiment, the operator may manually control every single movement. In an additional embodiment, the operator may control movements by selecting buttons that correspond to preprogrammed maneuvers, such as: change altitude, change speed, go to a desired longitude and/or latitude, return "home", and more.

At step 348, based on observed data, the UAV and/or a computing system (such as computing system 118 of FIG. 1) determines whether a potential subject, i.e., human, has been detected. The UAV continues flying until a potential subject has been detected. In an embodiment, components on board the UAV continuously transmit signals to the computing system. As noises and/or images are captured using microphone(s) and/or camera(s) onboard the UAV, the system continuously monitors for sounds and images that indicate the presence of a human (or potential subject).

When it is determined that a potential subject has been located, at step 352 the UAV attempts to capture an audio signal of the monitored subject using an onboard microphone (such as microphone 108 of FIG. 1).

At step 354, the voice analysis module, located within the processor, attempts to authenticate an identity of the monitored subject, as described above. For example, the voice analysis module compares the captured voiceprint against the voiceprint database in order to identify and/or authenticate the voice of a criminal, fugitive, missing person, and/or any other person of interest. If the identity of the monitored subject is not authenticated, subject monitoring method 300 returns to step 342. If the identity of the monitored subject is authenticated, at step 356 the UAV transmits either the current GPS coordinates of the UAV or estimated GPS coordinates of the monitored subject, i.e., the identified criminal, fugitive, missing person, and/or any other person of interest based on the GPS coordinates of the UAV. At step 358, a payload carried on board the UAV is deployed.

In an embodiment, the estimated GPS coordinates of the monitored subject are determined/estimated based on the GPS coordinates of the UAV and at least one other data point. Additional data points may include, for example: camera angle, camera direction, camera zoom, measured voice signal strength, triangulated coordinates based on the UAV position and other geographic features in the surrounding area, digital maps having GPS coordinates, or sonar pulses. In an embodiment, the estimated GPS coordinates of the monitored subject are determined after receiving, at a computing system, the GPS coordinates of the UAV and the angle, direction, and zoom of camera used to capture a facial image of the monitored subject. The computing system compares the received data against GPS coordinates associated with the general geographic location using a map to estimate the monitored subject's location. In an additional embodiment, the estimated GPS coordinates may be calculated on board the UAV.

Figure 4:
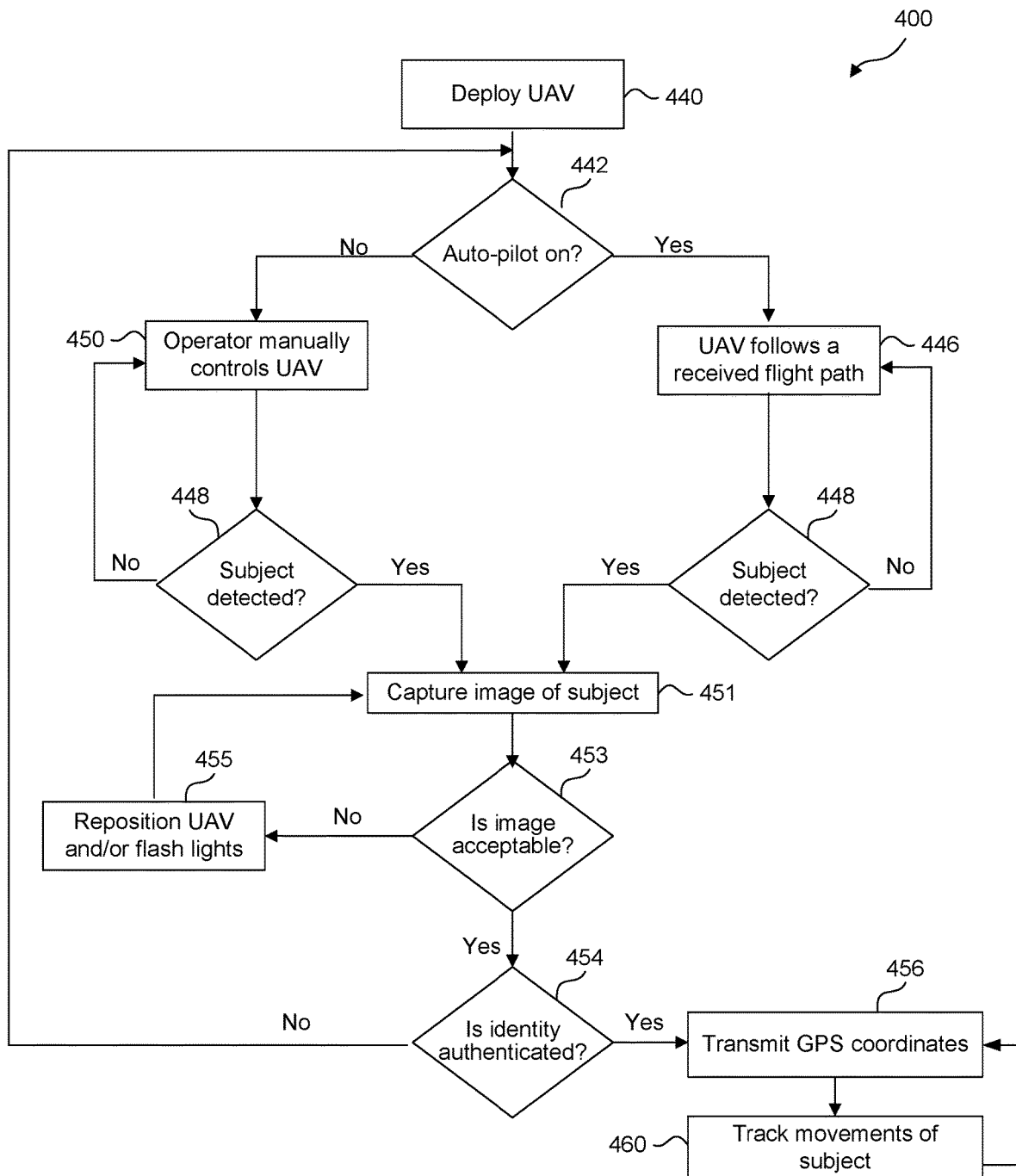
FIG. 4 depicts a flow chart diagram of an exemplary method for locating and tracking a person of interest, using a UAV.

FIG. 4 illustrates method 400, a method for locating and tracking a person of interest, using a UVA. At step 440, the UAV is deployed. As described above, the UAV may be deployed by launching the UAV and/or preparing to launch the UAV.

At step 442, it is determined whether the UAV is in auto-pilot mode or whether it is in manual operation mode. If the UAV is in auto-pilot mode, at step 444, the UAV follows a received pre-programmed auto-pilot flight path. As mentioned above, the auto-pilot flight path may include geographic obstacles that the UAV must negotiate around. Additionally, the auto-pilot flight path may include a "swath" path, where the UAV will fly in pre-determined lines in order to fly over a specific plot of land. At any time, an operator may interrupt the auto-pilot flight and begin operating the UAV in manual operation mode (not illustrated in FIG. 4). For example, when the UAV is flying in auto-pilot mode and an operator would like to observe something from a different distance, angle, or for a longer period of time, he or she may take control of the UAV. In an embodiment, the pilot may press a button or sequence of buttons to initialize a new pre-programmed flight maneuver. Further, the operator (or pilot) may modify the programmed flight path at any time during operation. At any time, the operator may return the UAV to auto-pilot mode and the UAV returns to the GPS location where the operator interruption took place and resume the predetermined flight path.

Now returning to step 442. If at step 442, the UAV has been deployed in manual operation mode, the operator controls of the UAV. At step 450, the operator (or pilot) controls the movements of the UAV using input/output devices through the user interface.

At step 448, based on observed data, the UAV and/or a computing system determines whether a potential subject, i.e., human, has been detected.

When it is determined that a potential subject has been located, at step 451 the UAV attempts to capture an image, video, and/or live feed of the monitored subject using an onboard camera (such as camera 110 of FIG. 1). At step 453, the facial recognition module, located within the, determines whether the captured image is of sufficient quality in order to authenticate the monitored subject's identity. If the captured image, video, or live feed does not meet the quality needed, at step 455 the UAV may be repositioned and additional mechanisms such as flashing lights and/or noised may be used to entice the monitored subject to look at the UAV. Subject monitoring method 400 then returns to step 451.

If at step 453 it is determined that the image, video, and/or live feed is sufficient, the facial recognition module attempted to authenticate an identity of the monitored subject, as described above. For example the facial recognition module may identify and/or authenticated the facial image of a criminal, fugitive, missing person, and/or any other person of interest by comparing the captured image(s) against stored images. If the identity of the monitored subject is not authenticated, subject monitoring method 400 returns to step 342. If at step 453 the identity of the monitored subject is authenticated, at step 456 the UAV transmits the estimated GPS coordinates of the monitored subject. In an embodiment not shown, at step 456, the UAV may alternatively transmit the current GPS coordinates of the UAV. At step 460, the UAV tracks the movements of the identified monitored subject and continues to transmit the updated coordinate estimates of the monitored subject as he/she moves relative to the UAV. In an embodiment the UAV transmits the updated coordinates continuously. In an additional embodiment the UAV transmits the updated coordinates at pre-determined intervals. In an embodiment, the UAV transmits the current GPS coordinates of the UAV as it tracks the monitored subject.

Various example, non-limiting embodiments, of contemplated monitoring system implementations shall now be discussed.

Figure 5:
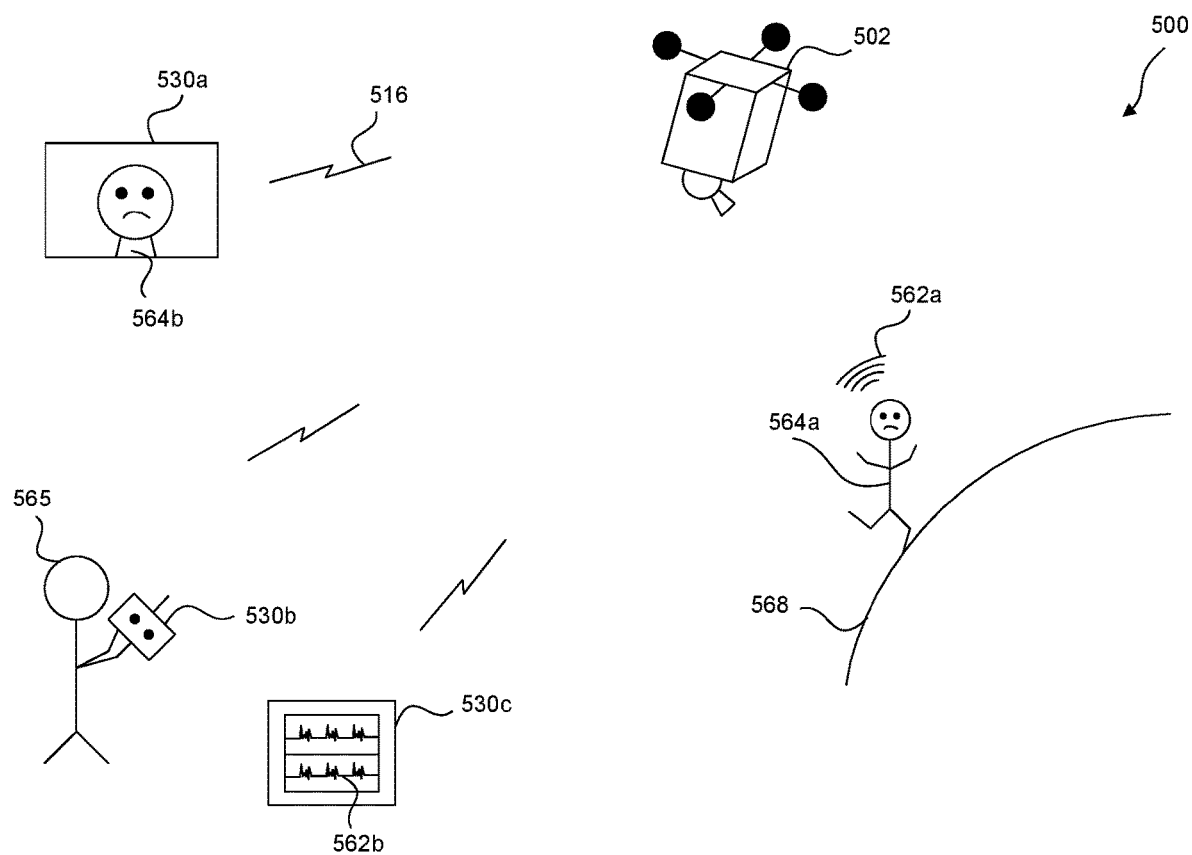
FIG. 5 depicts an exemplary method for authenticating the identity of a person of interest, using UAV.

FIG. 5 illustrates a method for authenticating the identity of a persona of interest 500, useful for illustrating various embodiments of the present disclosure.

As illustrated in FIG. 5, UAV 502 is controlled by operator 565 using input/output devices (not labeled) on user interface 530*b* over communications link 516. Monitored subject 564*a*, i.e., person of interest, is traversing geographic terrain 568. As illustrated, monitored subject 564*a* may be a search and rescue team member, a fugitive, a known criminal, a law enforcement officer in need of supplies, a missing person, a person of interest, a kidnapped child, or any other person. As the monitored subject traverses the terrain, the UAV captures a facial image of monitored subject as well as voice signals 562*a*.

Upon capturing the images and voice signals, UAV 502 transmits the captured data to a computing system (not labeled) and a corresponding processor (not labeled) over communications link 516.

A facial recognition module (such as facial recognition module 126 of FIG. 1 or facial recognition module 226 of FIGS. 2A and 2B) analyzes captured image 564*b* (or faceprint), while the captured image is displayed on user interface 530*a*. A voice analysis module (such as voice analysis module 124 of FIG. 1 or facial recognition module 224 of FIGS. 2A and 2B) converts the captured voice signals into digital files and analyze digital voice signals 562*b* (or voiceprints), while the voice signal analysis is displayed on user interface 530*b*.

Figure 6:
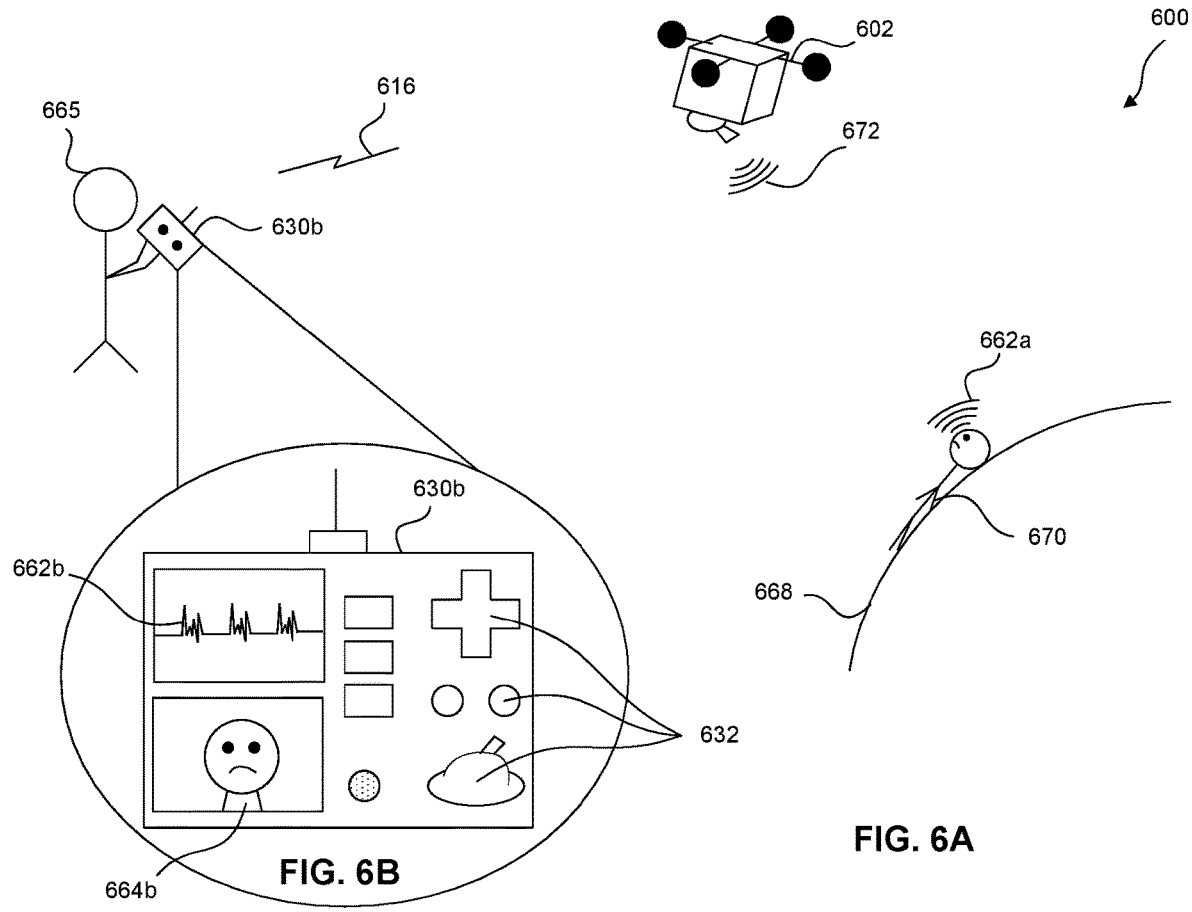
FIGS. 6A-6B depict an exemplary methods for authenticating the identity of a person of interest, using a UAV.

FIG. 6A illustrates a method for authenticating the identity of a persona of interest 600, useful for illustrating various embodiments of the present disclosure.

As illustrated in FIG. 6A, operator 665 controls UAV 602 with user interface 630*b* over communications link 616. As illustrated, monitored subject 670*a* may be a fugitive, a known criminal, a law enforcement officer in need of supplies, a missing person, a person of interest, a kidnapped child, an injured rescuer, and injured hiker, or any other person. As the monitored subject lies on the terrain, the UAV captures a facial image of monitored subject as well as voice signals 662*a*. Further illustrated, the UAV broadcasts voice signals 672. Voice signals 672 may include: a voice message from the operator (or pilot), a pre-recorded message requesting the monitored subject turn him or herself in to the authorities, a conversation taking place between the operator and the monitored subject, or any other audio signal appropriate for the occasion. For example, in an embodiment where the monitored subject 670 is a law enforcement officer seeking additional supplies (such as more ammunition, a firearm, etc.) the UAV may ask the monitored subject specific questions and/or require a voiceprint password in order to authenticate the identity of the subject before, for example, deploying the payload, i.e., ammunition, firearm, etc.

Upon capturing the images and voice signals, UAV 602 transmits the captured data to a computing system (not labeled) and a corresponding processor (not labeled) over communications link 616.

FIG. 6B illustrates a method for authenticating the identity of a persona of interest 630*b*, useful for illustrating various embodiments of the present disclosure. User interface 630*b* comprises a number of input/output devices 632 for controlling various functional features of a monitoring system. For example, in an embodiment, a joystick is used to control the direction, location, and/or movement of the UAV.

Facial recognition module 126 or facial recognition module 226 analyze captured image 664*b*, while user interface 630*b* displays the captured image.

Voice analysis module 124 or voice module 224 converts the captured voice signals into digital files (and/or voiceprints) and analyze digital voice signals 662*b*, while the user interface 530*b* displays the voice signal analysis.

Figure 7:
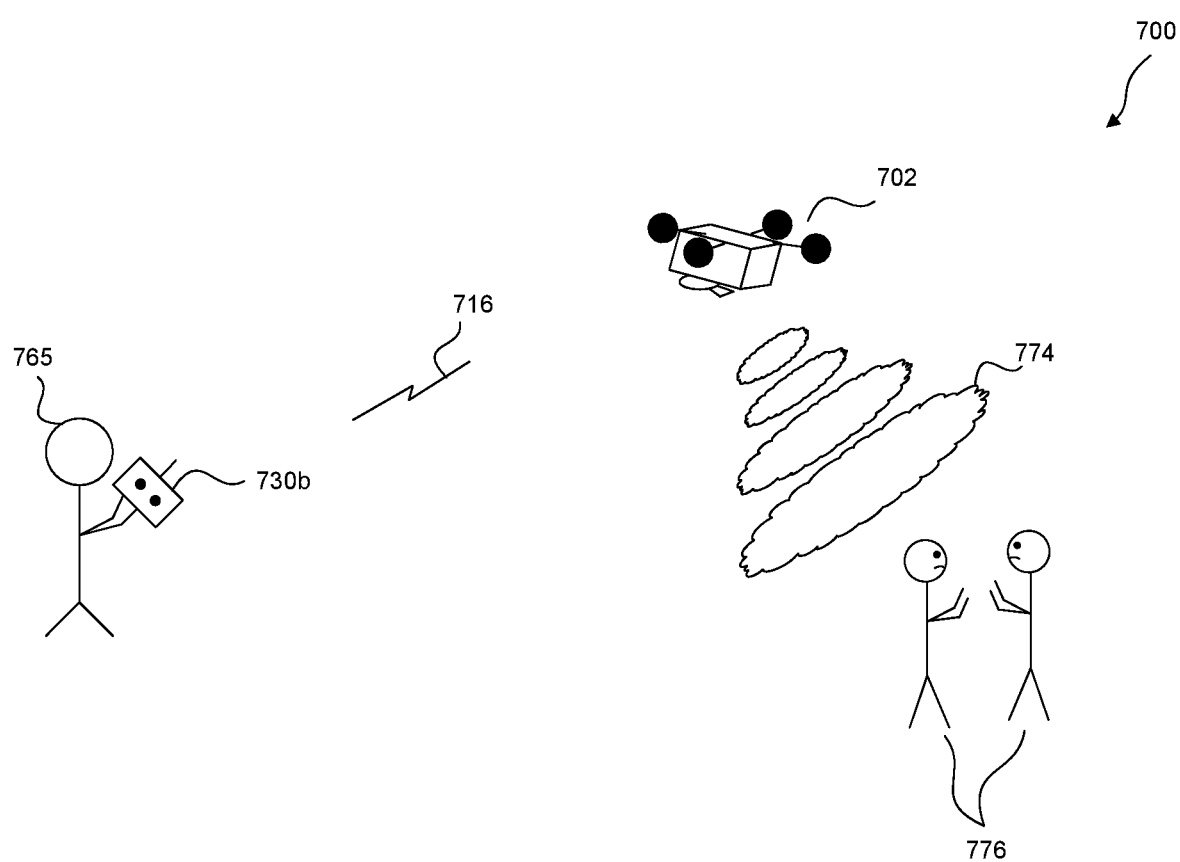
FIG. 7 depicts an exemplary method for authenticating the identity of a person of interest, using a UAV.

As illustrated in FIG. 7, operator 765 controls UAV 702 using input/output devices (not labeled) on user interface 730*b* over communications link 716. As illustrated, monitored subjects 776 may include: inmates fighting in the prison yard, known criminals engaging in a drug exchange, or any other suspicious activity. As the monitored subjects engage in the suspicious behavior, the UAV captures a facial image of monitored subject as well as voice signals.

Upon capturing the images and voice signals, UAV 702 transmits the captured data to a computing system (not labeled) and a corresponding processor (not labeled) over communications link 716. At the occurrence of a detected event, or at the command of the operator (or pilot), the payload deployment module causes the UAV to deploy an onboard payload. As illustrated, the payload may be pepper spray or tear gas. In other embodiments, where the payload is a projectile (such as rubber bullets, bean-bags, or other non-lethal ammunition) the UAV may fire the projectile toward monitored subjects 776. In an embodiment where the payload is a deployable canister (such as tear gas, a flash canister, or pepper spray), the UAV may release and/or activate at, or near, monitored subjects 776.

It is to be appreciated that the Detailed Description section, and not the Summary and Abstract sections (if any), is intended to be used to interpret the claims. The Summary and Abstract sections (if any) may set forth one or more but not all exemplary embodiments of the invention as contemplated by the inventor(s), and thus, are not intended to limit the invention or the appended claims in any way.

While the invention has been described herein with reference to exemplary embodiments for exemplary fields and applications, it should be understood that the invention is not limited thereto. Other embodiments and modifications thereto are possible, and are within the scope and spirit of the invention. For example, and without limiting the generality of this paragraph, embodiments are not limited to the software, hardware, firmware, and/or entities illustrated in the figures and/or described herein. Further, embodiments (whether or not explicitly described herein) have significant utility to fields and applications beyond the examples described herein.

Embodiments have been described herein with the aid of functional building blocks illustrating the implementation of specified functions and relationships thereof. The boundaries of these functional building blocks have been arbitrarily defined herein for the convenience of the description. Alternate boundaries can be defined as long as the specified functions and relationships (or equivalents thereof) are appropriately performed. Also, alternative embodiments may perform functional blocks, steps, operations, methods, etc. using orderings different than those described herein.

References herein to "one embodiment," "an embodiment," "an example embodiment," or similar phrases, indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of persons skilled in the relevant art(s) to incorporate such feature, structure, or characteristic into other embodiments whether or not explicitly mentioned or described herein.

The breadth and scope of the invention should not be limited by any of the above-described exemplary embodiments, but should be defined only in accordance with the following claims and their equivalents.

What is claimed is:

1. An unmanned aerial vehicle performing operations, the unmanned aerial vehicle comprising:
    a global positioning system receiver configured to determine a first global position of the unmanned aerial vehicle;
    a communication port configured to communicate with one or more computing systems over a communication link;
    a biometric sensing device; and
    a processor in communication with the global positioning system receiver, the communication port, and the biometric sensing device, wherein the processor is configured to:
        receive, over the communication link from a steering module implemented in the one or more computing systems, directional commands configured to cause the unmanned aerial vehicle to:
        operate in an auto-pilot mode in a programmed flight path until a potential subject is detected;
        interrupt the auto-pilot mode and cause the unmanned aerial vehicle to switch to a manual mode when the potential subject is detected, wherein the unmanned aerial vehicle operating in the manual mode comprises:
            detecting a GPS location of the unmanned aerial vehicle upon switching to the manual mode; and
            receiving additional directional commands to cause the unmanned aerial vehicle to deviate from the programmed flight path; and
        return to the auto-pilot mode after completion of the manual mode, wherein returning to the auto-pilot mode comprises returning to the GPS location of the unmanned aerial vehicle and resuming the programmed flight path;
        monitoring by the one or more computing systems, while the unmanned aerial vehicle is operating in the auto-pilot mode or the manual mode, at least one of a noise signal or a video signal for a presence of a potential target subject;
        transmit by the unmanned aerial vehicle, over the communication link to a biometric module implemented in the one or more computing systems while the unmanned aerial vehicle is operating in the auto-pilot mode or the manual mode, a biometric signal captured by the biometric sensing device, wherein the transmitting occurs in response to the monitoring; and
        receive by the unmanned aerial vehicle, over the communication link from a payload deployment module implemented in the one or more computing systems while the unmanned aerial vehicle is operating in the auto-pilot mode or the manual mode, a payload deployment command.

2. The unmanned aerial vehicle of claim 1, wherein the processor is further configured to:
    transmit, over the communication link to the one or more computing systems, an event signal indicative of a predetermined event, wherein the payload deployment command is received in response to transmitting the event signal.

3. The unmanned aerial vehicle of claim 1, wherein the directional commands comprise at least one of a real-time route, a GPS coordinate, an auto-pilot travel route, one or more commands to avoid an obstacle in a path of the unmanned aerial vehicle.

4. The unmanned aerial vehicle of claim 1, wherein the biometric signal comprises at least one of a voice signal or an image signal.

5. The unmanned aerial vehicle of claim 1, wherein the one or more computing systems comprises a first computing system, a second computing system, and a third computing system, wherein the steering module is implemented on the first computing system, the biometric module is implemented on the second computing system, and the payload deployment module is implemented on the third computing system, and wherein the directional commands are received from the first computing system, the biometric signal is transmitted to the second computing system, and the payload deployment command is received from the third computing system.

6. The unmanned aerial vehicle of claim 1, wherein monitoring at least one of the noise signal or the video signal for the presence of the potential target subject comprises:
    capturing an audio signal of the potential target subject; and
    authenticating the potential target subject based on the audio signal.

7. The unmanned aerial vehicle of claim 6, wherein in response to authenticating the potential target subject, the processor is configured to:
    estimate a GPS coordinate of the potential target subject based on a current GPS coordinate of the unmanned aerial vehicle and at least one of a camera angle, a camera direction, measured voice signal strength, and a triangulated coordinate based on the current GPS coordinate; and
    transmit the estimated GPS coordinate to the one or more computing systems.

8. A method for operating an unmanned aerial vehicle in communication with one or more computing systems over a communication link, the method comprising:

receiving, over the communication link from a steering module implemented in the one or more computing systems, a directional command configured to cause the unmanned aerial vehicle to:
operate in an auto-pilot mode in a programmed flight path until a potential subject is detected;
interrupt the auto-pilot mode and cause the unmanned aerial vehicle to switch to a manual mode when the potential subject is detected, wherein the unmanned aerial vehicle operating in the manual mode comprises:
detecting a GPS location of the unmanned aerial vehicle upon switching to the manual mode; and
receiving additional directional commands to cause the unmanned aerial vehicle to deviate from the programmed flight path; and
return to the auto-pilot mode after completion of the manual mode, wherein returning to the auto-pilot mode comprises returning to the GPS location of the unmanned aerial vehicle and resuming the programmed flight path;
monitoring by the one or more computing systems, while the unmanned aerial vehicle is operating in the auto-pilot mode or the manual mode, at least one of a noise signal or a video signal for a presence of a potential target subject;
transmitting by the unmanned aerial vehicle, over the communication link to a biometric module implemented in the one or more computing systems while the unmanned aerial vehicle is operating in the auto-pilot mode or the manual mode, a biometric signal captured by a biometric sensing device of the unmanned aerial vehicle, wherein the transmitting occurs in response to the monitoring; and
receiving by the unmanned aerial vehicle, over the communication link from a payload deployment module implemented in the one or more computing systems while the unmanned aerial vehicle is operating in the auto-pilot mode or the manual mode, a payload deployment command.

9. The method of claim 8, wherein the method further comprises:
transmitting, over the communication link to the one or more computing systems, an event signal indicative of a predetermined event, wherein the payload deployment command is received in response to transmitting the event signal.

10. The method of claim 8, wherein the directional command comprises at least one of a real-time route, a GPS coordinate, an auto-pilot travel route, one or more commands to avoid an obstacle in a path of the unmanned aerial vehicle.

11. The method of claim 8, wherein the biometric signal comprises at least one of a voice signal or an image signal.

12. The method of claim 8, wherein the one or more computing systems comprises a first computing system, a second computing system, and a third computing system, wherein the steering module is implemented on the first computing system, the biometric module is implemented on the second computing system, and the payload deployment module is implemented on the third computing system, and wherein the directional command is received from the first computing system, the biometric signal is transmitted to the second computing system, and the payload deployment command is received from the third computing system.

13. The method of claim 8, wherein monitoring at least one of the noise signal or the video signal for the presence of the potential target subject comprises:
capturing an audio signal of the potential target subject; and
authenticating the potential target subject based on the audio signal.

14. The method of claim 13, wherein in response to authenticating the potential target subject, the method further comprises:
estimating a GPS coordinate of the potential target subject based on a current GPS coordinate of the unmanned aerial vehicle and at least one of a camera angle, a camera direction, measured voice signal strength, and a triangulated coordinate based on the current GPS coordinate; and
transmitting the estimated GPS coordinate to the one or more computing systems.

15. A non-transitory computer-readable medium having instructions stored therein, which when executed by a processor in an unmanned aerial vehicle in communication with one or more computing systems over a communication link cause the processor to perform operations, the operations comprising:
receiving, over the communication link from a steering module implemented in the one or more computing systems, a directional command configured to cause the unmanned aerial vehicle to:
operate in an auto-pilot mode in a programmed flight path until a potential subject is detected;
interrupt the auto-pilot mode and cause the unmanned aerial vehicle to switch to a manual mode when the potential subject is detected, wherein the unmanned aerial vehicle operating in the manual mode comprises:
detecting a GPS location of the unmanned aerial vehicle upon switching to the manual mode; and
receiving additional directional commands to cause the unmanned aerial vehicle to deviate from the programmed flight path; and
return to the auto-pilot mode after completion of the manual mode, wherein returning to the auto-pilot mode comprises returning to the GPS location of the unmanned aerial vehicle and resuming the programmed flight path;
monitoring by the one or more computing systems, while the unmanned aerial vehicle is operating in the auto-pilot mode or the manual mode, at least one of a noise signal or a video signal for a presence of a potential target subject;
transmitting by the unmanned aerial vehicle, over the communication link to a biometric module implemented in the one or more computing systems while the unmanned aerial vehicle is operating in the auto-pilot mode or the manual mode, a biometric signal captured by a biometric sensing device, wherein the transmitting occurs in response to the monitoring; and
receiving by the unmanned aerial vehicle, over the communication link from a payload deployment module implemented in the one or more computing systems while the unmanned aerial vehicle is operating in the auto-pilot mode or the manual mode, a payload deployment command.

16. The non-transitory computer-readable medium of claim 15, wherein the operations further comprise:
transmitting, over the communication link to the one or more computing systems, an event signal indicative of a predetermined event, wherein the payload deployment command is received in response to transmitting the event signal.

17. The non-transitory computer-readable medium of claim 15, wherein the directional command comprises at least one of a real-time route, a GPS coordinate, an autopilot travel route, one or more commands to avoid an obstacle in a path of the unmanned aerial vehicle.

18. The non-transitory computer-readable medium of claim 15, wherein the biometric signal comprises at least one of a voice signal or an image signal.

19. The non-transitory computer-readable medium of claim 15, wherein the one or more computing systems comprises a first computing system, a second computing system, and a third computing system, wherein the steering module is implemented on the first computing system, the biometric module is implemented on the second computing system, and the payload deployment module is implemented on the third computing system, and wherein the directional command is received from the first computing system, the biometric signal is transmitted to the second computing system, and the payload deployment command is received from the third computing system.

20. The non-transitory computer-readable medium of claim 15, wherein monitoring at least one of the noise signal or the video signal for the presence of the potential target subject comprises:
   capturing an audio signal of the potential target subject; and
   authenticating the potential target subject based on the audio signal.

* * * * *